(12) United States Patent
Shimada et al.

(10) Patent No.: US 11,672,707 B2
(45) Date of Patent: Jun. 13, 2023

(54) METHOD FOR MANUFACTURING DISPOSABLE WORN ARTICLE

(71) Applicant: ZUIKO CORPORATION, Osaka (JP)

(72) Inventors: Takahiro Shimada, Osaka (JP); Daisuke Furukawa, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 0 days.

(21) Appl. No.: 17/789,233

(22) PCT Filed: Dec. 11, 2020

(86) PCT No.: PCT/JP2020/046276
§ 371 (c)(1),
(2) Date: Jun. 27, 2022

(87) PCT Pub. No.: WO2021/140831
PCT Pub. Date: Jul. 15, 2021

(65) Prior Publication Data
US 2023/0037404 A1    Feb. 9, 2023

(30) Foreign Application Priority Data

Jan. 10, 2020  (JP) .............................. JP2020-002647

(51) Int. Cl.
*A61F 13/15* (2006.01)

(52) U.S. Cl.
CPC .. *A61F 13/15699* (2013.01); *A61F 13/15593* (2013.01); *A61F 13/15739* (2013.01); *A61F 13/15764* (2013.01); *A61F 13/15804* (2013.01)

(58) Field of Classification Search
CPC .......................................... A61F 2013/15886
See application file for complete search history.

(56) References Cited

U.S. PATENT DOCUMENTS 9,089,453 B2 * 7/2015 McCabe ........... A61F 13/15699
2012/0247661 A1   10/2012 Ogasawara et al.
(Continued)

FOREIGN PATENT DOCUMENTS

JP    2011-83547 A    4/2011
JP    2012-45317 A    3/2012
(Continued)

OTHER PUBLICATIONS

International Search Report for corresponding Application No. PCT/JP2020/046276, dated Mar. 2, 2021.

*Primary Examiner* — Barbara J Musser
(74) *Attorney, Agent, or Firm* — Renner, Otto, Boisselle & Sklar, LLP

(57) ABSTRACT

The method of the present invention includes the steps of: arranging a plurality of non-continuous sheets of a predetermined length intermittently and successively in the conveyance direction on the continuous sheet so that the continuous elastic members are sandwiched between the non-continuous sheets and the continuous sheet; in an overlapping area where the non-continuous sheets overlap with the continuous sheet, attaching the continuous sheet and the non-continuous sheets to each other by welding the sheets to each other in a predetermined pattern, thus producing a continuous laminate; and in a non-overlapping area where the non-continuous sheets do not overlap with the continuous sheet, heating the continuous sheet in the same pattern as said pattern.

8 Claims, 6 Drawing Sheets

(56) References Cited

U.S. PATENT DOCUMENTS

2013/0213570 A1    8/2013  Iida
2016/0324694 A1   11/2016  Umebayashi
2016/0331600 A1*  11/2016  Polidori ............ A61F 13/15739

FOREIGN PATENT DOCUMENTS

| JP | 2013-255624 A | 12/2013 |
| JP | 2016-209277 A | 12/2016 |
| WO | 2013/080852 A1 | 6/2013 |
| WO | 2015/115462 A1 | 8/2015 |
| WO | 2019/188562 A1 | 10/2019 |

* cited by examiner

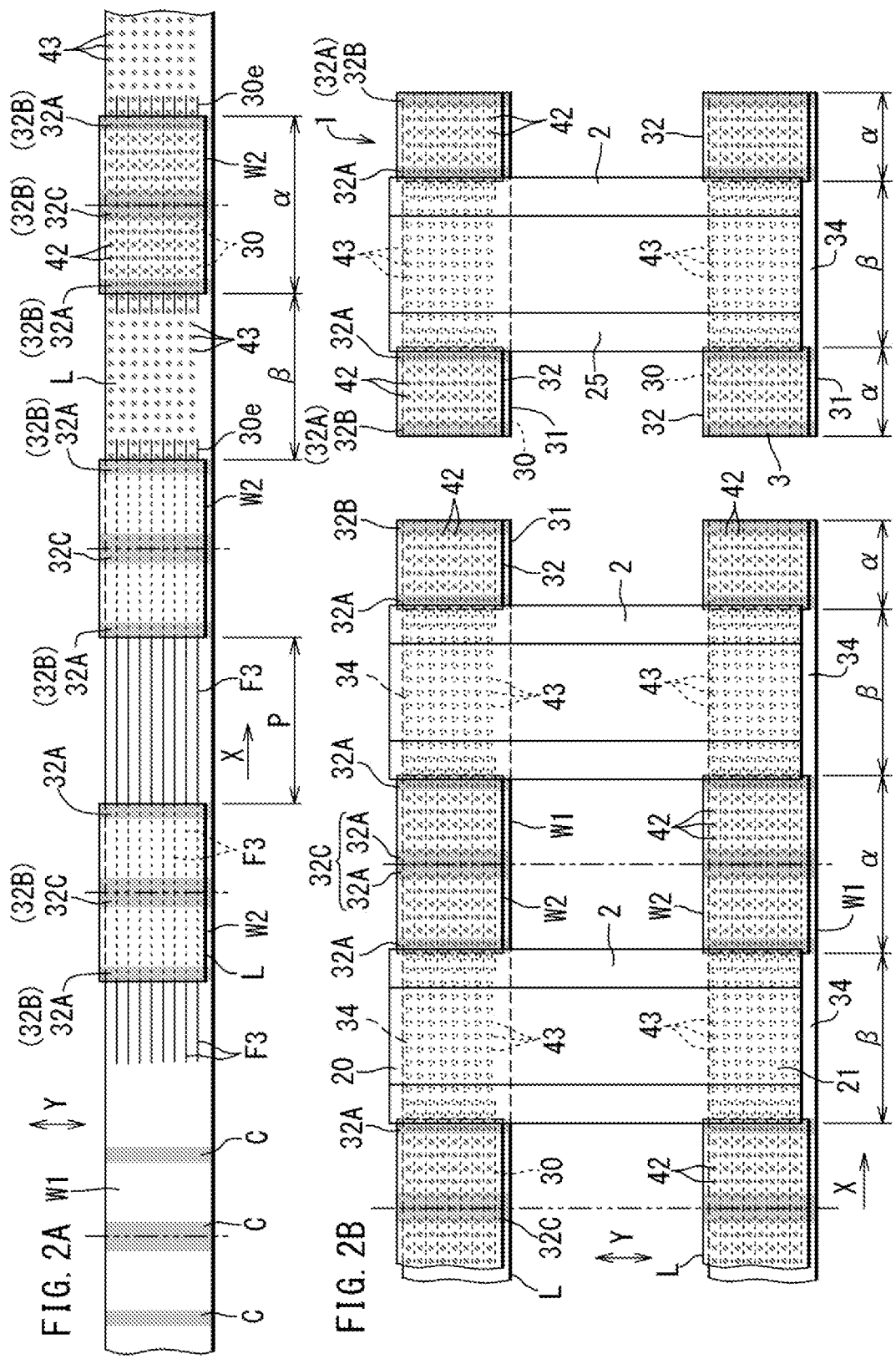

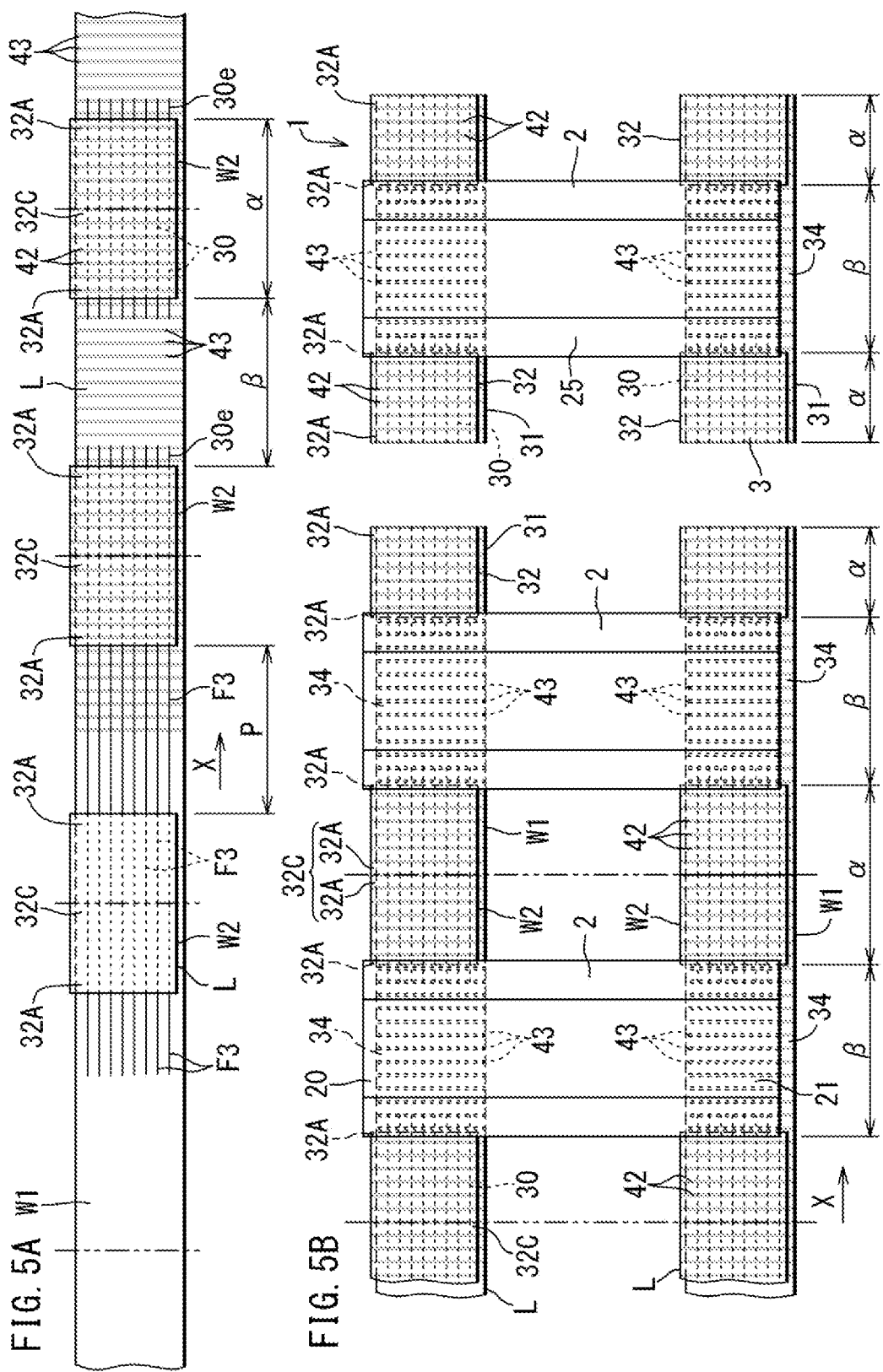

METHOD FOR MANUFACTURING DISPOSABLE WORN ARTICLE

TECHNICAL FIELD

The present invention relates to a method for manufacturing worn articles such as disposable pants and disposable diapers.

BACKGROUND ART

The invention of the first patent document identified below is a method for manufacturing an around-torso member (external portion) covering the torso of the wearer, wherein non-continuous sheets are arranged intermittently on a continuous sheet, with continuous elastic members sandwiched between the sheets, and the sheets welded to each other. An absorbent body is arranged in the non-overlapping area where the non-continuous sheets are absent. Therefore, the continuous elastic members are severed so that the contraction force of the elastic members does not act on the non-overlapping area.

CITATION LIST

Patent Document

[FIRST PATENT DOCUMENT] WO 2015/115462 (front page)

SUMMARY OF INVENTION

According to the invention of the prior document identified above, the sheets are welded to each other in a predetermined dot pattern, etc. However, since this welding is not done in the non-overlapping area, when the size of the worn article is changed, the pattern of welding by the sealing device also needs to be changed.

Thus, it is an object of the present invention to provide a method for manufacturing disposable worn articles, with which there is no need to change the pattern of welding even when the size is changed.

A method for manufacturing a disposable worn article of the present invention includes the steps of:

conveying one continuous sheet W1 that is continuous in a conveyance direction X;

arranging a plurality of continuous elastic members F3, which are continuous in the conveyance direction X of the continuous sheet W1, on the continuous sheet W1 while the continuous elastic members F3 are stretched;

arranging a plurality of non-continuous sheets W2 of a predetermined length intermittently and successively in the conveyance direction X on the continuous sheet W1 so that the continuous elastic members F3 are sandwiched between the non-continuous sheets W2 and the continuous sheet W1;

in an overlapping area α where the non-continuous sheets W2 overlap with the continuous sheet W1, attaching the continuous sheet W1 and the non-continuous sheets W2 to each other by welding the sheets W1, W2 to each other in a predetermined pattern, thus producing a continuous laminate L; and in a non-overlapping area β where the non-continuous sheets W2 do not overlap with the continuous sheet W1, heating the continuous sheet W1 in the same pattern as said pattern.

According to the present invention, welded portions 42 formed in the overlapping area α where the sheets overlap with each other and heating marks 43 formed in the non-overlapping area β where the non-continuous sheets W2 do not overlap with the continuous sheet W1 are formed in the same pattern on the continuous laminate L. Therefore, the welded portions 42 and the heating marks 43 of continuous laminates L produced before and after the size change are in the predetermined pattern. As a result, there is no need to change the welding pattern even when the size is changed.

Moreover, the pattern of the welded portions 42 and the pattern of the heating marks 43 appear to be the same in the overlapping area α and in the non-overlapping area β. Thus, the texture of the worn article is improved.

In the present invention, the pattern may be any of various patterns such as a dot pattern, a lattice pattern and a stripe pattern. The "same pattern" means not only that the patterns are of the same type, but also that the size, the pitch of arrangement, etc., of the dots or the lattice are the same in the overlapping area α and in the non-overlapping area β.

BRIEF DESCRIPTION OF THE DRAWINGS

FIG. 1A, FIG. 1B and FIG. 1C each show a worn article according to Embodiment 1 of the present invention, wherein FIG. 1A is a schematic perspective view showing, flattened, the article as seen from a diagonally forward direction, and FIG. 1B and FIG. 1C are cross-sectional views taken along line IB-IB and line IC-IC, respectively, of FIG. 1A.

FIG. 2A and FIG. 2B are each a schematic perspective view showing an example of a method for manufacturing the worn article.

FIG. 4A, FIG. 4B and FIG. 4C each show a worn article according to Embodiment 2 of the present invention, wherein FIG. 4A is a schematic perspective view showing, flattened, the article as seen from a diagonally forward direction, and FIG. 4B and FIG. 4C are cross-sectional views taken along line IVB-IVB and line IVC-IVC, respectively, of FIG. 4A.

FIG. 5A and FIG. 5B are each a schematic perspective view showing an example of a method for manufacturing the worn article.

Figure 1A:
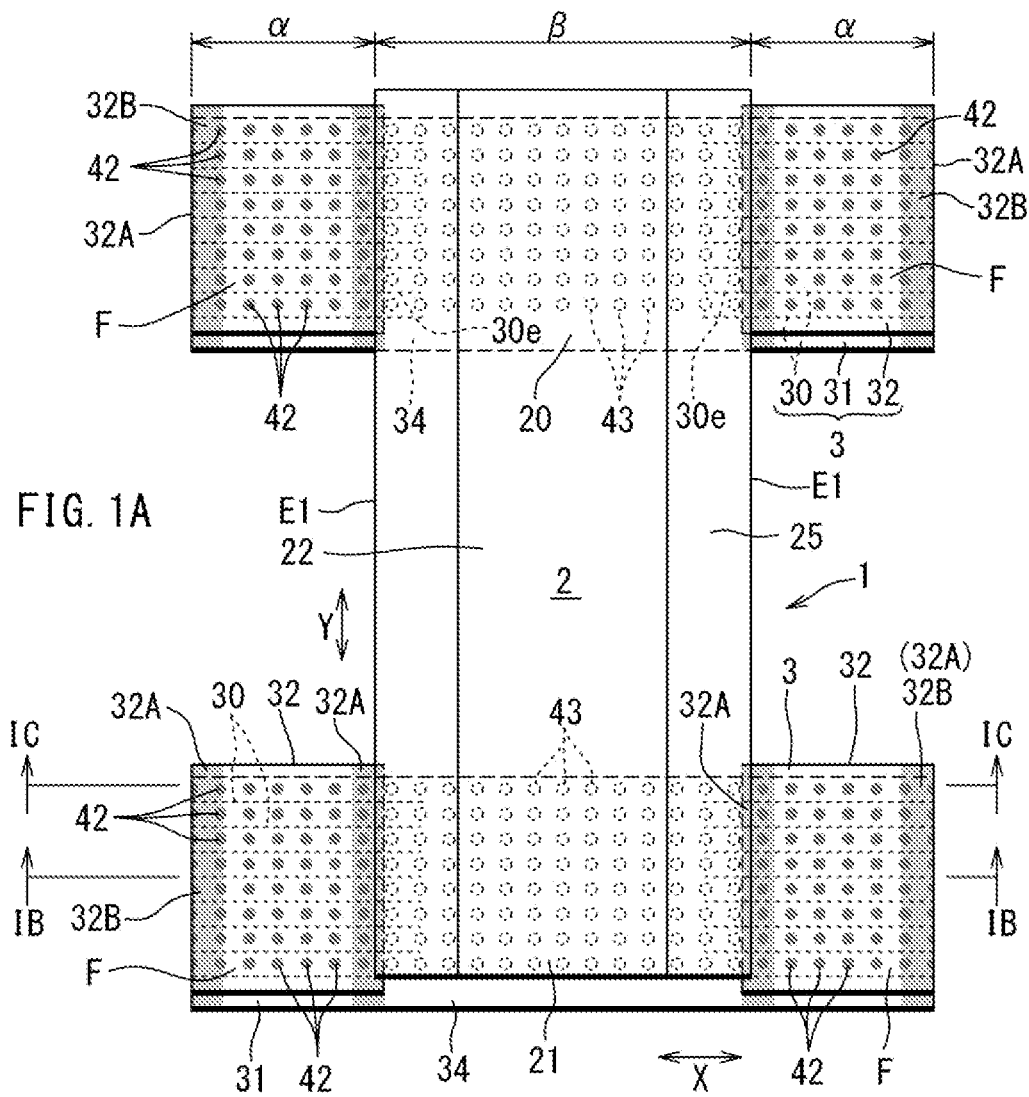

Note that FIG. 1A, FIG. 2A, FIG. 2B, FIG. 4A, FIG. 5A and FIG. 5B show perspective views in which sheets and non-woven fabrics are shifted from one another in the up-down direction of the drawing sheet so that it is easy to see how these members are laid on one another. In these figures, welded portions are colored in dark gray while bonded portions are colored in light gray.

DESCRIPTION OF EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

The structure of a worn article 1 according to Embodiment 1 of the present invention will now be described with reference to the drawings.

Figure 1B:
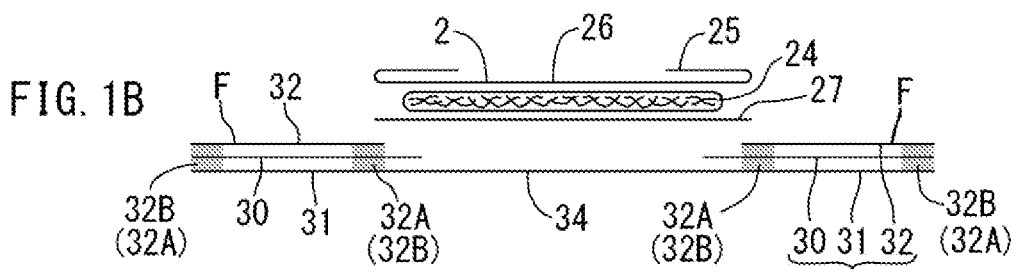

As shown in FIG. 1A and FIG. 1B, the worn article 1 includes an absorbent body 2 and a pair of, front and rear, around-torso members 3, 3. The absorbent body 2 includes a front portion 20, a back portion 21 and a crotch portion 22. The front portion 20 covers the front torso (the front portion of the torso) of the wearer and extends in the girth direction X. The back portion 21 covers the rear torso (the rear portion of the torso) of the wearer and extends in the girth direction X. The crotch portion 22 covers the crotch of the wearer between the front portion 20 and the back portion 21.

The crotch portion 22 is continuous with the front portion 20 and the back portion 21 and extends in the length (longitudinal) direction Y perpendicular to the girth direction X. The absorbent body 2 forms a part or whole of the crotch portion 22.

In FIG. 1A, the present worn article is put on with the crotch portion 22 folded in two along a virtual line that is parallel to the girth direction X. As a result, the end portions in the girth direction X of the front around-torso member 3 and the rear around-torso member 3 overlap with each other.

As shown in FIG. 1B, the absorbent body 2 is provided with an absorbent core 24. This absorbent core 24 absorbs body fluids. The absorbent core 24 is sandwiched between a top sheet 26 and a back sheet 27. The sheets 26, 27 and the absorbent core 24 are layered on each other.

In FIG. 1B, the top sheet 26 is made from a thin, liquid-permeable non-woven fabric and covers the skin-contact surface of the absorbent core 24. Cuffs 25 may be provided on this top sheet 26. The top sheet 26 consists of an essentially non-stretchable non-woven fabric.

In the present invention, the "skin-contact surface" refers to an inner surface that directly or indirectly contacts the skin of the wearer when the diaper is worn, and directly or indirectly opposes to the skin of the wearer.

The back sheet 27 covers the non-skin-contact surface of the absorbent core 24 and is made from a liquid-impermeable resin sheet. An exterior non-woven fabric (not shown) may be bonded and layered on the non-skin-contact surface of the back sheet 27.

In the present invention, the "non-skin-contact surface" refers to an outer surface, opposite to the skin-contact surface, that does not contact the skin of the wearer when the diaper is worn, and does not oppose the skin of the wearer.

In FIG. 1A, the absorbent body 2 is provided to bridge between the front around-torso member 3 and the rear around-torso member 3. That is, the front portion 20, which is one end portion of the absorbent body 2 in the length direction Y, is bonded to the front around-torso member 3. On the other hand, the back portion 21, which is the other end portion of the absorbent body 2 in the length direction Y, is bonded to the rear around-torso member 3.

The front and rear around-torso members 3 each form a pair of a front flap F and a rear flap F, protruding in the girth direction X from the absorbent body 2, the flaps F each forming a part of the front and rear around-torso portions. That is, as shown in FIG. 1A, each flap F protrudes in the girth direction X relative to the crotch portion 22 and extends out in the girth direction X from the opposite edges E1 of the absorbent body 2 (the crotch portion 22).

The front and rear around-torso members 3 are formed by severing a continuous laminate L (FIG. 2A) to be described below.

As shown in FIG. 1B, the around-torso members 3 are made from a laminate including elastic members 30, the first and second sheets 31 to 32 layered on each other.

The first sheet 31 and a pair of the second sheets 32 are made from an air-permeable nonwoven fabric. The first sheet 31 extends continuously in the girth direction X from the front or the rear torso of the wearer to the opposite end portions. On the other hand, the pair of second sheets 32, 32 are absent in the front torso and the rear torso, but are arranged layered on the first sheet 31 and spaced apart from each other in the girth direction X so that they are arranged in the opposite end portions.

The elastic members 30 are sandwiched between the first sheet 31 and the second sheets 32 and are stretchable in the girth direction X. The elastic members 30, the second sheets 32 and the first sheet 31 are layered on each other in the area of the front and rear flaps F as clearly shown in FIG. 1B. Therefore, the flaps F are three-layered.

The elastic members 30 are severed in front and rear torso portions 34 between the pair of second sheets 32, 32 spaced apart from each other in the girth direction X. That is, as shown in FIG. 1B, in the central portion between the pair of second sheets 32, 32, the first sheet 31 and the back sheet 27 are layered on each other with no elastic members 30 sandwiched therebetween. Thus, the contraction force of the elastic members 30 is not exerted in the front and rear torso portions 34 between the pair of second sheets 32, 32.

As shown in FIG. 1A, in the present embodiment, one end portion 30e of the severed elastic members 30 protrudes from the second sheet 32 toward the front and rear torso portions 34.

The elastic members 30 are used to fit the around-torso members 3 to the wearer. For example, as the elastic members 30, a plurality of rubber threads, rubber tapes, or a thread-shaped or tape-shaped material including a thermoplastic resin (hotmelt) may be employed.

When rubber threads are employed as the elastic members 30, attachment portions 32B are formed by applying an adhesive only on the end portion 32A in the girth direction X of the second sheet 32 of FIG. 1B, instead of applying an adhesive across the entire surface of the first sheet 31 and the second sheet 32. In these attachment portions 32B, the first sheet 31 and the second sheet 32 may sandwich the elastic members 30 therebetween and may be attached together, thereby forming a laminate. The attachment portions 32B of FIG. 1A extend in the length direction Y and are spaced apart from each other in the girth direction X. One end portion 30e of the severed elastic members 30 protrudes from the attachment portions 32B toward the center in the girth direction X of the torso portion 34. Note that the bonded areas with an adhesive are colored in light gray in figures.

In FIG. 1A, in the overlapping area α where the second sheet 32 overlaps with the first sheet 31, they are attached together by being partially welded together in the welded portions 42 as indicated by a large number of small circles of FIG. 1A and a large number of small crosses of FIG. 10. In the case of the present embodiment, in the flaps F of FIG. 1A, the first sheet 31 and the second sheet 32 are attached together, between adjacent elastic members 30, in a plurality of welded portions 42 intermittently along the stretch direction X of the elastic members 30.

Figure 1C:
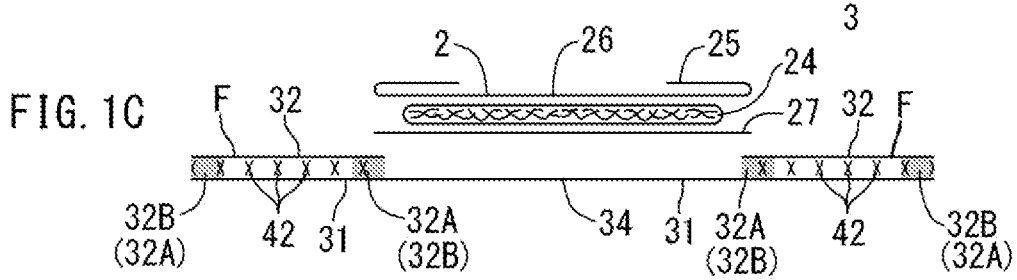

That is, in this case, the first sheet 31 is welded to the second sheet 32 only in portions of the first sheet 31 as the welded portions 42 are indicated by xxx in FIG. 1C. Note that in FIG. 1A, FIG. 2A and FIG. 2C, the welded portions 42 are colored in dark gray.

On the other hand, in the non-overlapping area β of the first sheet 31 where the second sheet 32 does not overlap with the first sheet 31 of FIG. 1A, a large number of heating marks 43 appear as indicated by a broken line in FIG. 1A. These heating marks 43 and welded portions 42 are visually perceived as patterns from the side of the non-skin-contact surface of the worn article 1. Note that a heating mark 43 refers to a mark that results from alteration of a heated portion of a non-woven fabric, and this does not need to be melted.

These welded portions 42 and heating marks 43 are formed in dot patterns, which are identical to each other. Thus, the aesthetic appearance of the worn article 1 is improved.

The dot pattern may be arranged in a regular matrix pattern, arranged so as to form a predetermined pattern, or may be random. Moreover, the pattern may be other than dots.

The dots, i.e., the welded portions 42 and the heating marks 43, may be small circles or may be other shapes such as squares, or the dots may be two or more different shapes such as a mixture of circles and squares.

In FIG. 1A, the absorbent body 2 is provided to bridge between the front torso portion 34 and the rear torso portion 34, where the second sheet 32 is absent. In this embodiment, the absorbent body 2 is arranged so as to at least partially cover (overlap with) the end portions 32A, 32A of the pair of second sheets 32, 32.

The absorbent body 2 may be formed with around-leg portions, which are narrowed so as to conform to the legs of the wearer. Other elastic members made from rubber threads, or the like, for example, may be provided in the around-leg portions or in areas of the around-torso member 3 that are continuous with the around-leg portions so as to conform to the legs of the wearer.

When the worn article is a diaper, a male touch fastener (not shown) may be secured to the skin-contact surface of the rear around-torso member 3, and a female touch fastener may be secured to the non-skin-contact surface of the front around-torso member 3.

Note that a tape material coated with a fastening agent may be used instead of a male touch fastener, in which case a surface to which the fastening agent is likely to stick needs to be formed on the front around-torso member 3, etc.

When the worn article is of the pants type, the end portions of the front flap F and the rear flap F in the girth direction X may be welded together.

Next, a method for manufacturing the present worn article will be described with reference to FIG. 2.

The continuous sheet W1 of FIG. 2A to be the first sheet 31 of FIG. 1 is continuous in the conveyance direction X along the girth direction X and is conveyed in the conveyance direction X. While being conveyed, an adhesive C is applied by an applicator 64 (FIG. 3A) to areas of the continuous sheet W1 that correspond to the attachment portions 32B. Note that the continuous sheet W1 and a non-continuous sheet W2 to be described below are both made from an air-permeable non-woven fabric.

On the other hand, a plurality of continuous elastic members F3 of FIG. 2A, which are to be a plurality of elastic members 30 of FIG. 1, are arranged on the continuous sheet W1 while being stretched. Each continuous elastic member F3 is continuous in the conveyance direction X of the continuous sheet W1.

At the same time, a plurality of non-continuous sheets W2 of FIG. 2A are arranged one after another intermittently in the conveyance direction X on the continuous sheet W1. They are arranged so that the opposite edges and the central portion of the non-continuous sheets W2 in the conveyance direction X overlap with areas where the adhesive C is applied. Thus, the continuous elastic members F3 are sandwiched between the non-continuous sheets W2 and the continuous sheet W1, thus forming the continuous laminate L as will be described below. The non-continuous sheet W2 is later severed in two as shown in FIG. 2B, thus providing the second sheets 32.

When the continuous sheet W1, the continuous elastic members F3 and the non-continuous sheets W2 are layered on each other as shown in FIG. 2A, the continuous sheet W1, the non-continuous sheets W2 and the continuous elastic members F3 are attached together by the adhesive C in the attachment portions 32B where the adhesive C is applied. That is, in the attachment step, the continuous sheet W1, the non-continuous sheets W2 and the continuous elastic members F3 are attached together intermittently in the conveyance direction X in a plurality of attachment portions 32B extending in the width direction Y that crosses the conveyance direction X in areas where the non-continuous sheets W2 are arranged. The attachment portions 32B extend across the continuous laminate L.

In the attachment step, the attachment portions 32B are formed in the opposite end portions 32A of the non-continuous sheet W2 in the conveyance direction X and in the central portion 32C spaced apart from the opposite end portions 32A and between the opposite end portions 32A. The attachment can be made in the attachment portions 32B by heat seal or ultrasonic seal between the continuous sheet W1 and the non-continuous sheets W2. The width of the attachment portion 32B in the conveyance direction X in the central portion 32C is greater than the width of the attachment portion 32B in the conveyance direction X in the opposite end portions 32A.

Then, the continuous laminate L is supplied to a cutter (not shown) to sever the continuous elastic members F3 between intermittently-arranged non-continuous sheets W2, W2 that are adjacent to each other. By this severing, the contraction force from the continuous elastic members F3 is removed, and a plurality of elastic members 30 are produced, which are non-continuous in the conveyance direction X.

By the severing, the opposite ends of the elastic members 30 are exposed at the end of the non-continuous sheet W2.

Note that the method for severing the continuous elastic members F3 on the continuous sheet W1 is disclosed in, for example, U.S. Pat. No. 7,438,779 B2, the entire content of which is herein incorporated by reference.

In the welding step after the attachment step, in the overlapping area α where the non-continuous sheets W2 are arranged on the continuous sheet W1, the continuous sheet W1 and the non-continuous sheets W2 are attached to each other in a plurality of welded portions 42 along the stretch direction X of the elastic members F3 and intermittently. In the case of the present embodiment, the welding step may be performed by forming a plurality of welded portions 42 between two elastic members 30 adjacent to each other, and the welded portions 42 may be formed while being aligned in the stretch direction X and in the width direction Y.

Note that while FIG. 2A shows only one continuous laminate L for the sake of illustration, a pair of continuous laminates L, L parallel to each other may be formed in practice as shown in FIG. 2B.

That is, in the welding step, in the overlapping area α where the non-continuous sheets W2 overlap with the continuous sheet W1, the sheets W1, W2 are attached to each other by welding the continuous sheet W1 and the non-continuous sheets W2 to each other in a predetermined dot pattern, thus producing the continuous laminate L. This welding may be ultrasonic welding, which will be described below, or thermal welding (heat seal) using a heat roller.

On the other hand, in the non-overlapping area β where the non-continuous sheets W2 do not overlap with the continuous sheet W1, the continuous sheet W1 is heated in the same dot pattern as the dot pattern described above. By this heating, the heating marks 43 of the same dot pattern as the dot pattern of the welded portions 42 described above are formed on the continuous sheet W1 in the non-overlapping area β.

Figure 3A:
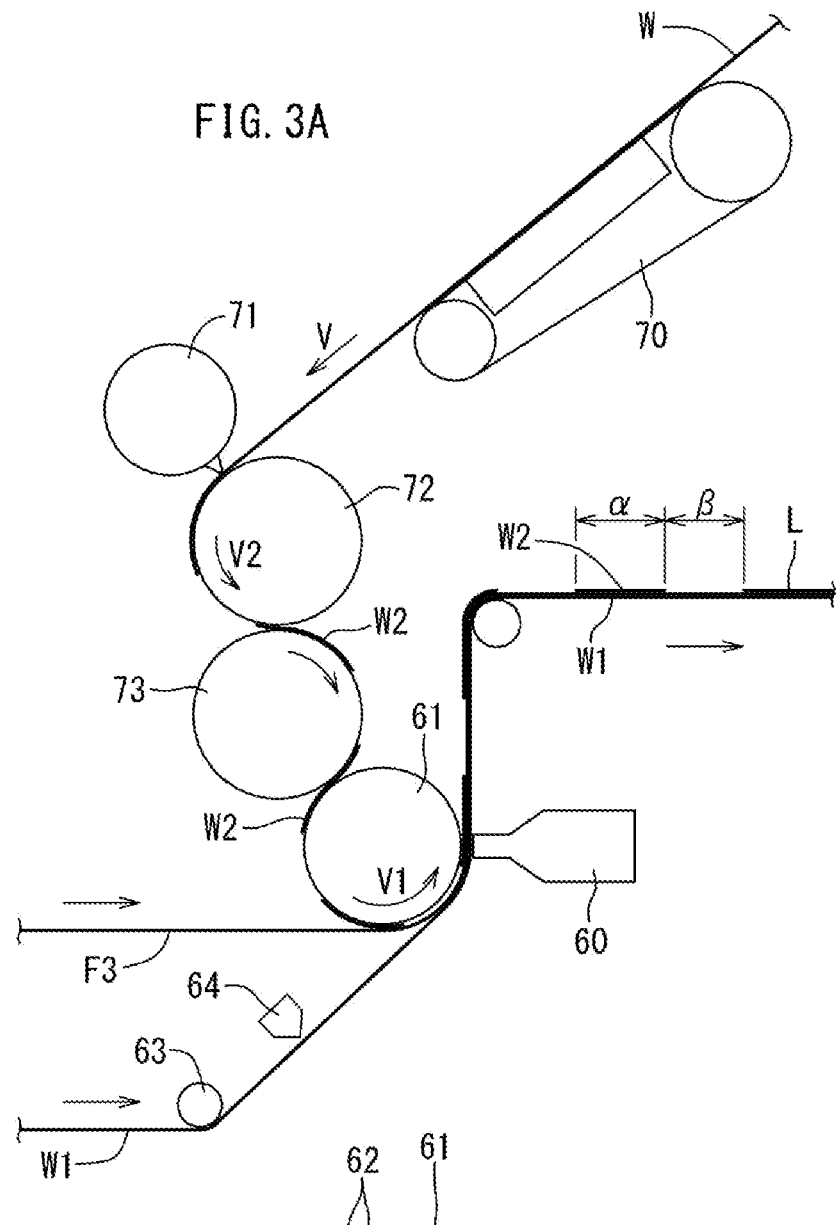
FIG. 3A is a schematic layout view showing an example of a manufacturing device for manufacturing a continuous laminate L of the embodiment.
Figure 3B:
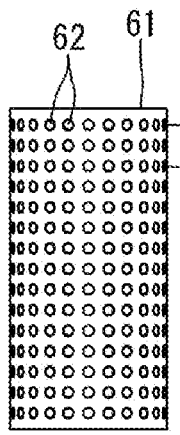
FIG. 3B is a front view of the first anvil roll.

The heating and the welding are performed on a single first anvil roll 61 (FIG. 3B).

A plurality of absorbent bodies 2 are intermittently arranged one after another on the pair of continuous laminates L, L of FIG. 2B, wherein the front portions 20 and the back portions 21 of the absorbent bodies 2 in the longitudinal direction Y are arranged one after another with each absorbent body 2 provided to bridge between the front and rear torso portions 34, 34, i.e., on the continuous sheet W1 between the non-continuous sheets W2 adjacent to each other in the conveyance direction X.

After the bridging, in order to obtain individual worn articles 1, the continuous laminate L is successively severed along a virtual severing line extending in the width direction Y in the central portion 32C between adjacent absorbent bodies 2, 2. That is, the continuous sheet W1, the elastic members 30 and the non-continuous sheets W2 are severed along the virtual severing line extending in the width direction Y perpendicular to the conveyance direction X. Thus, the central portion 32C becomes a pair of end portions 32A.

Note that after the severing, individual worn articles 1 are folded in two along the absorbent body 2, thereby producing diaper-type or pants-type worn articles 1.

Next, an example of a device for manufacturing the around-torso member 3 of the worn article 1 will be described.

In FIG. 3A, the first anvil roll 61 is arranged so as to oppose a horn 60 for ultrasonic heating. A large number of projections 62 shown in FIG. 3B are formed on the first anvil roll 61. The horn 60 of FIG. 3A ultrasonically vibrates to heat the continuous laminate L between the horn 60 and the first anvil roll 61, thereby forming the welded portions 42 and the heating marks 43 (FIG. 2A). These may be formed intermittently in the girth direction X and/or the longitudinal direction Y of the continuous laminate L.

Note that the first anvil roll 61 conveys one continuous sheet W1 at the circumferential velocity V1.

One continuous sheet W1, the non-continuous sheets W2 and the continuous elastic members F3, which together form the continuous laminate L, are introduced onto the circumference of the first anvil roll 61 of FIG. 3A. These sheets and members introduced are welded together as described above in the overlapping area α between the sheets W1, W2 by the horn 60 for ultrasonic heating and the first anvil roll 61. On the other hand, the non-overlapping area β of one continuous sheet W1 is subjected only to heating, thereby forming the heating marks 43 (FIG. 2A).

An introduction roller 63 for introducing one continuous sheet W1 is arranged upstream of the first anvil roll 61. The applicator 64 for applying an adhesive to one continuous sheet W1 is provided on the path of one continuous sheet W1 between the introduction roller 63 and the first anvil roll 61.

Also, the present manufacturing device is provided with a conveyor 70, a second anvil roll 72, a cutter 71, etc., for producing the non-continuous sheet W2 from another continuous sheet W.

The conveyor 70 conveys the other continuous sheet W while sucking on the other continuous sheet W while controlling so that the conveying velocity V onto the second anvil roll 72 is constant. The second anvil roll 72 rotates at the circumferential velocity V2, which is higher than the conveying velocity V. On the second anvil roll 72, the cutter 71 successively severs the tip of the other continuous sheet W to successively produce the non-continuous sheets W2.

A velocity-changing device 73 for changing the supply velocity of the non-continuous sheet W2 is provided between the second anvil roll 72 and the first anvil roll 61. This velocity-changing device 73 may be a drum called a repitch drum well known in the art, for example. This repitch drum picks up the non-continuous sheet W2 from the second anvil roll 72 at the circumferential velocity V2, and hands over the non-continuous sheet W2 to the first anvil roll 61 at the supply velocity V1 of the first anvil roll 61.

Next, a method for manufacturing continuous laminates L for worn articles of different sizes will be described in detail.

In FIG. 3A, the other continuous sheet W is supplied at a constant conveying velocity V by the conveyor 70, and is conveyed at the circumferential velocity V2 of the second anvil roll 72 while slipping on the second anvil roll 72. The other continuous sheet W is severed intermittently and successively in the conveyance direction X by the cutter 71, thereby successively producing the non-continuous sheets W2. Non-continuous sheets W2, W2 adjacent to each other are subjected to the spacing step, in which the velocity thereof is changed by the velocity-changing device 73 so that the pitch thereof in the conveyance direction X is a predetermined pitch, and are handed over onto the first anvil roll 61 at the supply velocity V1.

Then, the conveying velocity of the non-continuous sheet W2 is changed so that the pitch P (FIG. 2A) between the non-continuous sheets W2, W2 that results from the spacing step varies between different types of worn articles. That is, the circumferential velocity V2 of the second anvil roll 72 for conveying the non-continuous sheet W2 and the pick-up velocity of the velocity-changing device 73 when picking up the non-continuous sheet W2 are changed.

For example, when manufacturing a worn article of a small size, the second anvil roll 72 of FIG. 3A conveys the non-continuous sheet W2 at a small conveying velocity so that the pitch P of FIG. 2A is equal to a small first pitch. That is, in this case, the circumferential velocity V2 is small, and the pitch P between the non-continuous sheets W2 of FIG. 2A becomes small.

On the other hand, when manufacturing a worn article of a large size, the second anvil roll 72 of FIG. 3A conveys the non-continuous sheet W2 at a conveying velocity that is higher than the small conveying velocity described above so that the pitch P of FIG. 2A is equal to the second pitch larger than the first pitch. That is, in this case, the circumferential velocity V2 is large, and the pitch P between the non-continuous sheets W2 of FIG. 2A becomes large.

Note that the circumferential velocity of the cutter 71 of FIG. 3A also changes in sync with the circumferential velocity V2 of the second anvil roll 72, and the length of the overlapping area α in the girth direction X is large when the pitch P of FIG. 2A is large, and the length of the overlapping area α in the girth direction X is small when the pitch P is small.

Now, the elastic members 30 may be attached by being welded to the two sheets 31, 32 by the welded portions 42 of FIG. 1A (e.g., WO 2016/208513). The pattern of the heating marks 43 and the welded portions 42 may be a continuous lattice pattern, or the like, instead of a dot pattern (ditto).

Figure 4A:
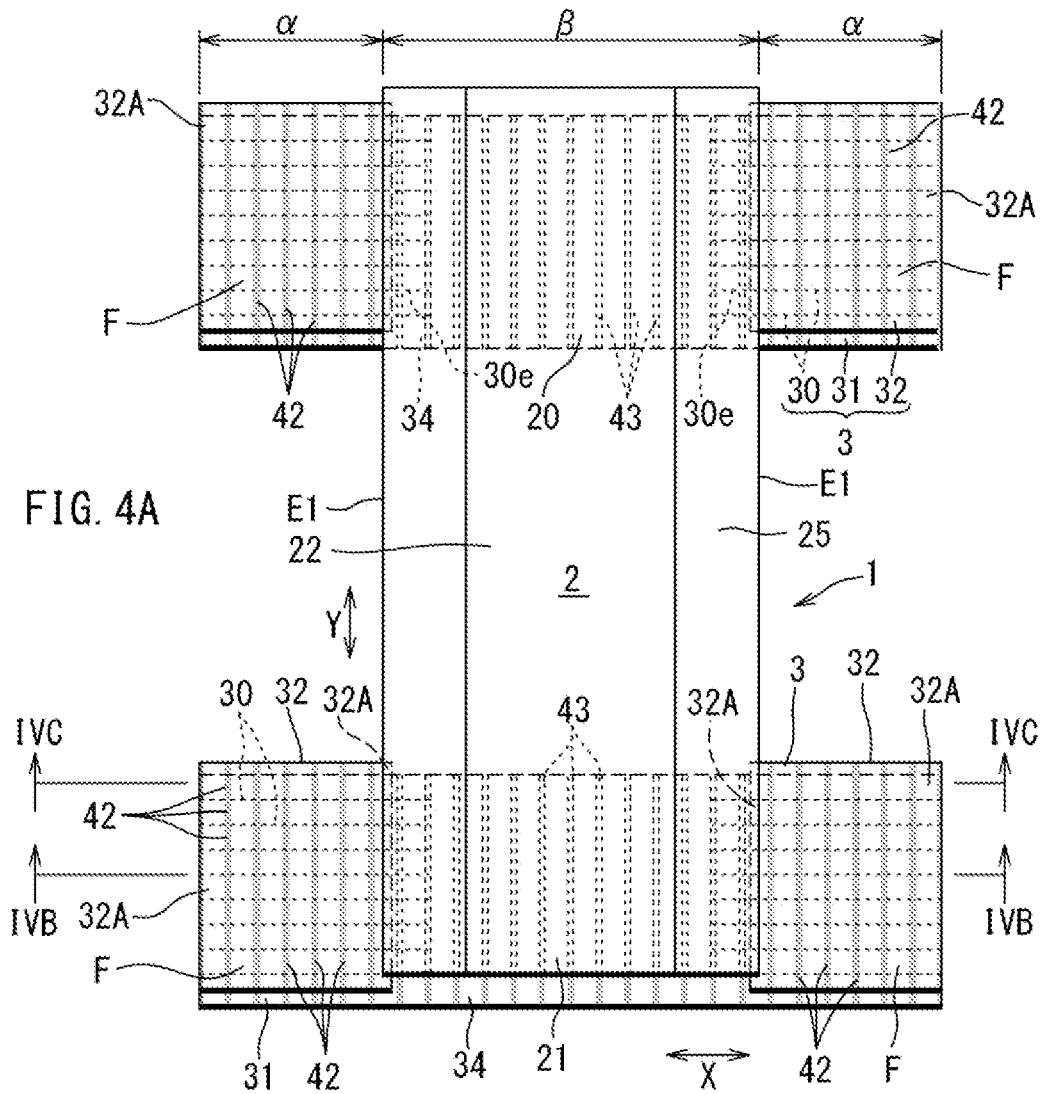
Figure 4B:
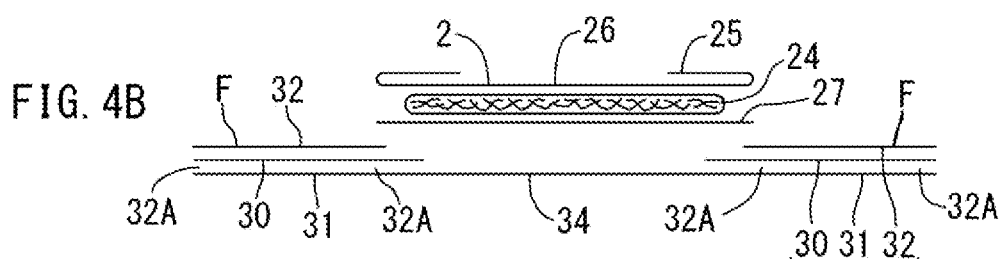
Figure 4C:
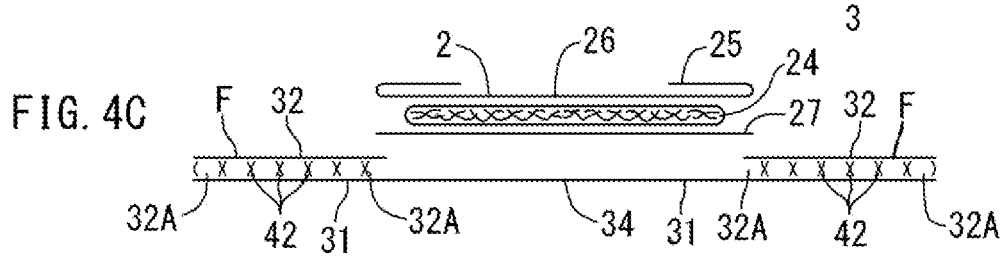

For example, as in the second embodiment of FIG. 4A and FIG. 5A and FIG. 5B, the pattern of the welded portions 42 and the heating marks 43 described above may be a stripe pattern. Also in such an embodiment, the welded portions 42 and the heating marks 43 are colored in dark gray.

This embodiment will be described below.

In FIG. 4A, the welded portions 42 and the heating marks 43 are provided intermittently in the girth direction X of the around-torso member 3, and extend across the entire width in the width direction Y. The welded portions 42 are provided also in the end portion 32A of the second sheet 32 to attach together the second sheet 32 and the first sheet 31.

That is, the welded portions 42 are provided also in the opposite end portions 32A, 32A of the non-continuous sheet W2, and these welded portions 42 are attached to the sheets 31, 32 with the elastic members 30 sandwiched between the first sheet 31 and the second sheet 32. Therefore, in this embodiment, there is no need for the attachment between the sheets 31, 32 with an adhesive.

In this embodiment, the worn article 1 is produced as shown in FIG. 5A and FIG. 5B. As can be seen from these figures, in this embodiment, there is no need for the step of bonding the non-continuous sheet W2 to one continuous sheet W1.

Figure 6A:
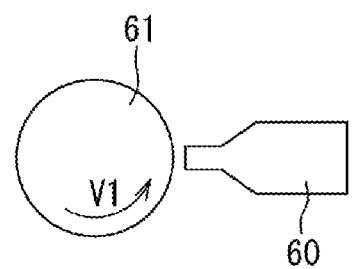
FIG. 6A is a side view showing the first anvil roll and a horn 60 of the embodiment.
Figure 6B:
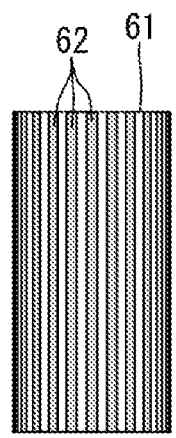
FIG. 6B is a front view of the first anvil roll.

Note that the projections 62 of the first anvil roll 61 of FIG. 6A and FIG. 6B used in this embodiment are formed as protrusions corresponding to the stripe described above. The pattern does not need to be uniform, but may be non-uniform, in the overlapping area α and the non-overlapping area β. Moreover, the heating marks 43, and the like, of the first embodiment of FIG. 1 may be in a square shape, etc., instead of a dot pattern.

Welding by heating may be heat seal using a heat roll, instead of heating by ultrasonic energy.

The specific embodiment described above primarily encompasses an invention comprising steps, etc., as shown below.

A method for manufacturing a worn article includes the steps of: conveying one continuous sheet W1 that is continuous in a conveyance direction X; arranging a plurality of continuous elastic members F3, which are continuous in the conveyance direction X of the continuous sheet W1, on the continuous sheet W1 while the continuous elastic members F3 are stretched; arranging a plurality of non-continuous sheets W2 of a predetermined length intermittently and successively in the conveyance direction X on the continuous sheet W1 so that the continuous elastic members F3 are sandwiched between the non-continuous sheets W2 and the continuous sheet W1: in an overlapping area α where the non-continuous sheets W2 overlap with the continuous sheet W1, attaching the continuous sheet W1 and the non-continuous sheets W2 to each other by welding the sheets W1, W2 to each other in a predetermined pattern, thus producing a continuous laminate L; and in a non-overlapping area β where the non-continuous sheets W2 do not overlap with the continuous sheet W1, heating the continuous sheet W1 in the same pattern as said pattern.

With the configuration described above, in the overlapping area α where the sheets overlap with each other and the non-overlapping area β where the non-continuous sheets W2 do not overlap with the continuous sheet W1, heating is done in the same pattern, thus forming the continuous laminate L. Therefore, continuous laminates L produced before and after the size change have heating marks in the predetermined pattern. As a result, there is no need to change the welding pattern even when the size is changed.

Moreover, the pattern of the welded portions 42 and the heating marks 43 appears to be the same in the overlapping area α and in the non-overlapping area β. Thus, the texture of the worn article is improved.

In a preferred embodiment, the method further includes: a severing step of severing another continuous sheet W different from the continuous sheet W1 intermittently and successively in the conveyance direction X, thereby obtaining the non-continuous sheets W2; and a spacing step of conveying the non-continuous sheets W2, W2 so that a pitch between the non-continuous sheets W2, W2 adjacent to each other in the conveyance direction X is equal to a predetermined pitch.

In this case, the continuous sheet W1 can be produced from the other continuous sheet W.

In a more preferred embodiment, the conveying velocity of the non-continuous sheets W2 is changed so that a pitch between the non-continuous sheets W2, W2 that results from the spacing step varies between different types of worn articles.

In this case, it is possible to change the pitch between the non-continuous sheets W2 in the girth direction X depending on the type of the worn article.

In a more preferred embodiment, the non-continuous sheets W2 are conveyed at a low conveying velocity so that the pitch therebetween is equal to a first small pitch when manufacturing a worn article of a small size, whereas the non-continuous sheets W2 are conveyed at a high conveying velocity so that the pitch therebetween is equal to a second pitch that is larger than the first pitch when manufacturing a worn article of a large size.

In this case, when the size of the worn article is small, the length of the around-torso member 3 is shorter, whereas when the size of the worn article is large, the length of the around-torso member 3 is longer. Therefore, it is possible to obtain the around-torso member 3 of an appropriate length according to the size.

Any feature illustrated and/or depicted in conjunction with one embodiment or preferred embodiments may be used in the same or similar form in one or more of the other embodiments, and/or may be used in combination with, or in place of, the other embodiments.

While preferred embodiments have been described above with reference to the drawings, obvious variations and modifications will readily occur to those skilled in the art upon reading the present specification.

For example, the worn article to be manufactured by the present manufacturing method may have a design pattern.

The worn article may be a T-shaped diaper. Thus, such variations and modifications shall fall within the scope of the present invention as defined by the appended claims.

INDUSTRIAL APPLICABILITY

The present invention is applicable to diaper-type and pants-type disposable worn articles and to a method for manufacturing the same.

REFERENCE SIGNS LIST

1: Worn article
2: Absorbent body, 20: Front portion, 21: Back portion, 22: Crotch portion
24: Absorbent core, 25: Cuff, 26: Top sheet, 27: Back sheet
3: Around-torso member, 30: Elastic member, 30e: End portion
31: First sheet, 32: Second sheet, 32A: End portion, 32B: Attachment portion, 32C: Central portion, 34: Front and rear torso portions
42: Welded portion, 43: Heating marks
60: Horn, 61: First anvil roll, 62: Projection
63: Introduction roller, 64: Applicator
70: Conveyor, 71: Cutter, 72: Second anvil roll, 73: Velocity-changing device
C: Adhesive, F: Front flap, L: Continuous laminate
X: Girth direction (conveyance direction), Y: Longitudinal direction (width direction)
F3: Continuous elastic member
W1: One continuous sheet, W2: Non-continuous sheet, W: Another continuous sheet
V: Conveying velocity, V1: Supply velocity, V2 Circumferential velocity
P: Pitch
α: Overlapping area, β: Non-overlapping area

The invention claimed is:

1. A method for manufacturing a worn article, comprising the steps of:
   conveying one continuous sheet W1 that is continuous in a conveyance direction X;
   arranging a plurality of continuous elastic members F3, which are continuous in the conveyance direction X of the continuous sheet W1, on the continuous sheet W1 while the continuous elastic members F3 are stretched;
   arranging a plurality of non-continuous sheets W2 of a predetermined length intermittently and successively in the conveyance direction X on the continuous sheet W1 so that the continuous elastic members F3 are sandwiched between the non-continuous sheets W2 and the continuous sheet W1;
   in an overlapping area α where the non-continuous sheets W2 overlap with the continuous sheet W1, attaching the continuous sheet W1 and the non-continuous sheets W2 to each other by welding the continuous sheet W1 and the non-continuous sheets W2 to each other in a predetermined pattern, thus producing a continuous laminate L; and
   in a non-overlapping area β where the non-continuous sheets W2 do not overlap with the continuous sheet W1, heating the continuous sheet W1 in the same pattern as the predetermined pattern.

2. The method according to claim 1, further comprising:
   a severing step of severing another continuous sheet W different from the continuous sheet W1 intermittently and successively in the conveyance direction X, thereby obtaining the non-continuous sheets W2; and
   a spacing step of conveying the non-continuous sheets W2, W2 so that a pitch between the non-continuous sheets W2, W2 adjacent to each other in the conveyance direction X is equal to a predetermined pitch.

3. The method according to claim 2, wherein the conveying velocity of the non-continuous sheets W2 is changed so that the pitch between the non-continuous sheets W2, W2 that results from the spacing step varies between different types of worn articles.

4. The method according to claim 3, wherein:
   the non-continuous sheets W2 are conveyed at a low conveying velocity so that the pitch therebetween is equal to a first small pitch when manufacturing a worn article of a small size,
   whereas the non-continuous sheets W2 are conveyed at a high conveying velocity so that the pitch therebetween is equal to a second pitch that is larger than the first pitch when manufacturing a worn article of a large size.

5. The method according to claim 1, wherein in an area where one of the non-continuous sheets W2 is arranged, the continuous elastic members F3 sandwiched between the continuous sheet W1 and the one of the non-continuous sheets W2 are attached to the continuous sheet W1 and the one of the non-continuous sheets W2 intermittently in the conveyance direction X in a plurality of areas extending in a width direction that crosses the conveyance direction X.

6. The method according to claim 2, wherein in an area where one of the non-continuous sheets W2 is arranged, the continuous elastic members F3 sandwiched between the continuous sheet W1 and the one of the non-continuous sheets W2 are attached to the continuous sheet W1 and the one of the non-continuous sheets W2 intermittently in the conveyance direction X in a plurality of areas extending in a width direction that crosses the conveyance direction X.

7. The method according to claim 3, wherein in an area where one of the non-continuous sheets W2 is arranged, the continuous elastic members F3 sandwiched between the continuous sheet W1 and the one of the non-continuous sheets W2 are attached to the continuous sheet W1 and the one of the non-continuous sheets W2 intermittently in the conveyance direction X in a plurality of areas extending in a width direction that crosses the conveyance direction X.

8. The method according to claim 4, wherein in an area where one of the non-continuous sheets W2 is arranged, the continuous elastic members F3 sandwiched between the continuous sheet W1 and the one of the non-continuous sheets W2 are attached to the continuous sheet W1 and the one of the non-continuous sheets W2 intermittently in the conveyance direction X in a plurality of areas extending in a width direction that crosses the conveyance direction X.

* * * * *